United States Patent
Fabis et al.

(10) Patent No.: US 12,139,703 B2
(45) Date of Patent: *Nov. 12, 2024

(54) LYSIS, BINDING AND/OR WASH REAGENT FOR ISOLATING AND/OR PURIFYING NUCLEIC ACIDS

(71) Applicant: Qiagen GmbH, Hilden (DE)

(72) Inventors: Roland Fabis, Leverkusen (DE); Anke Homann, Langenfeld (DE); Thorsten Voss, Leverkusen (DE); Thomas Hanselle, Hilden (DE)

(73) Assignee: QIAGEN GmbH, Hilden (DE)

( * ) Notice: Subject to any disclaimer, the term of this patent is extended or adjusted under 35 U.S.C. 154(b) by 602 days.

This patent is subject to a terminal disclaimer.

(21) Appl. No.: 17/235,403

(22) Filed: Apr. 20, 2021

(65) Prior Publication Data
US 2022/0002708 A1    Jan. 6, 2022

Related U.S. Application Data

(63) Continuation of application No. 15/440,682, filed on Feb. 23, 2017, now abandoned, which is a continuation of application No. 12/994,308, filed as application No. PCT/EP2009/056268 on May 25, 2009, now Pat. No. 9,617,532.

(30) Foreign Application Priority Data

May 30, 2008   (DE) .................. 10 2008 026 058.4

(51) Int. Cl.
C12N 15/10        (2006.01)
C12N 1/06         (2006.01)

(52) U.S. Cl.
CPC .......... *C12N 15/1006* (2013.01); *C12N 1/06* (2013.01); *C12N 15/1003* (2013.01)

(58) Field of Classification Search
CPC .. C12N 15/1006; C12N 1/06; C12N 15/1003; C12N 15/1013; C12Q 1/6806
See application file for complete search history.

(56) References Cited

U.S. PATENT DOCUMENTS

| | | |
|---|---|---|
| 5,932,422 A | 8/1999 | Shyjan et al. |
| 5,989,431 A | 11/1999 | Evans et al. |
| 6,383,393 B1 | 5/2002 | Colpan et al. |
| 7,109,322 B2 | 9/2006 | Colpan et al. |
| 7,510,826 B2 | 3/2009 | Colpan et al. |
| 7,776,542 B1 | 8/2010 | Aoyagi et al. |
| 9,617,532 B2 | 4/2017 | Fabis et al. |
| 2002/0081619 A1 | 6/2002 | Bastian et al. |
| 2003/0180936 A1* | 9/2003 | Memarzadeh ........... C12N 7/00 435/235.1 |
| 2004/0009496 A1* | 1/2004 | Eiblmaier ............... C07H 21/04 536/25.4 |
| 2004/0259162 A1 | 12/2004 | Kappel |
| 2005/0019769 A1 | 1/2005 | Lenz |
| 2005/0053962 A1 | 3/2005 | Blackburn et al. |
| 2005/0142570 A1 | 6/2005 | Parthasarathy |
| 2009/0047724 A1 | 2/2009 | Hillebrand |
| 2009/0048439 A1 | 2/2009 | Weisburg et al. |
| 2011/0054162 A1 | 3/2011 | Kim et al. |
| 2011/0076751 A1 | 3/2011 | Fabis et al. |

FOREIGN PATENT DOCUMENTS

| | | |
|---|---|---|
| DE | 101 47 439 A1 | 4/2003 |
| EP | 0 880 537 B1 | 12/2004 |
| EP | 1 932 913 B1 | 12/2007 |
| JP | 6205676 A | 7/1994 |
| JP | 2006-238854 A | 9/2006 |
| WO | 95/21849 A1 | 8/1995 |
| WO | 96/41810 A1 | 12/1996 |
| WO | 00/77235 A1 | 12/2000 |
| WO | 2006/023471 A2 | 3/2006 |
| WO | 2006/073497 A1 | 7/2006 |
| WO | 2007/060248 A1 | 5/2007 |
| WO | 2009/144182 A1 | 12/2009 |

OTHER PUBLICATIONS

Alves et al., "p-Nitrophenylphosphatase Activity Catalyzed by Plasma Membrane ($Ca^{2+}$ + $MG^{2+}$)ATPPase: Correlation with Structural Changes Modulated by Glycerol and $Ca^{2+}$," *Bioscience Reports* 21(1):25-32 (2001).

Applied Biosystems, "DNA Isolation from Fresh and Frozen Blood, Tissue Culture Cells, and Buccal Swabs," URL:http://www3.appliedbiosystems.com/cms/groups/mcb_support/documents/generaldocuments/cms_041387.pdf (55 pages) [retrieved on Feb. 7, 2012].

Bosenberg-Smith et al., "Assessment of DNA Yeild and Purity: an Overlooked Detail of PCR Troubleshooting," *Clinical Microbiology Newsletter* 33(1):1-6 (2012).

Byrnes et al., "A portable, pressure driven, room temperature nucleic acid extraction and storage system for point of care molecular diagnostics," *Analytical Methods* 5:3177-3184 (2013).

Cull et al., "[12] Preparation of Extracts from Prokaryotes," *Methods in Enzymology* 182:147-153, 1990.

Currie et al., "Oxidation of Self-Organized Nonionic Surfactants," *Langmuir* 20:3835-3837 (2004).

Genov et al., "Stability of subtilisins and related proteinases (subtilases)," *Int. J. Peptide Protein Res.* 45:391-400 (1995).

Johansson et al., "Brij 58, a polyoxyethylene acyl ether, creates membrane vesicles of uniform sidedness. A new tool to obtain inside-out (cytoplasmic side-out) plasma membrane vesicles," *The Plant Journal* 7(1): 165-173, 1995.

Kellermayer et al., "Release of Potassium, Lipids, and Proteins From Nonionic Detergent Treated Chicken Red Blood Cells," *Journal of Cellular Physiology* 159:197-204, 1994.

(Continued)

*Primary Examiner* — Yih-Horng Shiao
*Assistant Examiner* — Hoi Yan Lee
(74) *Attorney, Agent, or Firm* — Seed IP Law Group LLP

(57) ABSTRACT

The present invention relates to a lysis, binding and/or wash reagent for isolating and/or purifying nucleic acids and a method for isolating and/or purifying nucleic acids.

14 Claims, 2 Drawing Sheets

(56) References Cited

OTHER PUBLICATIONS

Kerwin, "Polysorbates 20 and 80 Used in the Formulation of Protein Biotherapeutics: Structure and Degradation Pathways," *Journal of Pharmaceutical Sciences* 97(8):2924-2935 (Aug. 2008).

Millipore Sigma Product Information Sheet for Triton® X-45, [online], [retrieved from the Internet on Feb. 11, 2021] (2021).

Millipore Sigma Product Information Sheet for IGEPAL® CA-520, [online], [retrieved from the Internet on Feb. 11, 2021] (2021).

Muller et al., "Maturation of Parvovirus LuIII in a Subcellular System. I. Optimal Conditions for in vitro Synthesis and Encapsidation of Viral DNA," *Journal of General Virology* 64:1043-1054, 1983.

Pandit et al., "Phase behavior of aqueous solutions containing nonionic surfactant-polyethylene glycol mixtures," *International Journal of Pharmaceutics* 122:27-33 (1995).

PCR clean-up Gel extraction, User Manuel, NucleoSPin® Gel and PCR Clean-up, Macherey-Nagel (Jan. 2012/Rev. 02).

Sabat et al., "New Method for typing *Staphylococcus aureus* Strains: Multiple-Locus Variable-No. Tandem Repeat Analysis of Polymorphism and Genetic Relationships of Clinical Isolates," *Journal of Clinical Microbiology* 41(4):1801-1804 (Apr. 2003).

The Ginas Project's G-SRS record for nonoxynol-9, Mar. 6, 2018 [online], [retrieved from the Internet on Oct. 10, 2018] (2018).

The Ginas Project G-SRS record for octoxynol-5, Mar. 6, 2018 [online], [retrieved from the Internet on Oct. 10, 2018] (2018).

* cited by examiner

LYSIS, BINDING AND/OR WASH REAGENT FOR ISOLATING AND/OR PURIFYING NUCLEIC ACIDS

CROSS REFERENCE TO RELATED APPLICATIONS

The present application is a continuation application of U.S. application Ser. No. 15/440,682 filed Feb. 23, 2017, which is a continuation of Ser. No. 12/994,308 filed Nov. 23, 2010, now issued as U.S. Pat. No. 9,617,532, which is a U.S. national phase application of PCT/EP2009/056268 filed May 25, 2009, which claims priority to DE Application No. 10 2008 026 058.4 filed May 30, 2008. U.S. application Ser. Nos. 12/994,308 and 15/440,682 are herein incorporated by reference in their entity.

FIELD OF THE INVENTION

The present invention relates to a lysis, binding and/or wash reagent and to a method for isolating and/or purifying nucleic acids. Said lysis, binding and/or wash reagent and method are particularly suitable for use purposes in molecular diagnostics.

BACKGROUND OF THE INVENTION

The prior art has disclosed a multiplicity of methods for isolating and/or purifying nucleic acids such as deoxyribonucleic acid (DNA) or ribonucleic acid (RNA) from cells, cell cultures or virus cultures.

In this context, "classical" methods for isolating nucleic acids, many of which are carried out manually, are based on a one-step method which involves carrying out an extraction after the addition of an aqueous buffer and an organic extractant. The nucleic acids remain in the aqueous phase and may be isolated after the organic phase which contains undesired accompanying substances has been removed.

These methods firstly use normally harmful organic extractants such as chloroform or phenol, and secondly water-soluble contaminants remain in the aqueous phase which contains the nucleic acids and need to be removed in further purification steps.

As a result, an alternative method has gained importance in the prior art, which is based on selective adsorption of nucleic acids to solid, mostly mineral supports such as silicon dioxide. The binding principle is based on a reversible binding of the nucleic acids under the influence of "chaotropic" salts and/or alcohol to the silicon dioxide surface. In a multi-step method, various solutions or mixtures, usually lysis, binding, wash and/or eluting solutions or mixtures, are added to the nucleic acid-containing sample, and in a final method step the purified nucleic acid is eluted from the support which has been added in the binding step at the latest.

The basic principle of both methods is based on the cells, in particular the plant, animal, human, bacterial or viral cells, being lysed in a first step. To this end, the cells are firstly incubated with a lysis buffer which disrupts the cells.

The prior art has disclosed buffers and methods for lysing cellular materials of a biological sample. Known lysis buffers frequently contain the surfactant polyoxyethylene sorbitan monolaurate (Tween® 20). This surfactant is used for converting contaminations into a soluble or stabilized state during cell lysis, in order to remove them from the nucleic acid.

Disadvantageously, lysis buffers containing polyoxyethylene sorbitan monolaurate (Tween® 20) are not stable during storage. For example, the pH decreases. A particular disadvantage is the fact that the yield of the isolated nucleic acids is reduced after storage when these lysis buffers are used. Another disadvantage is the fact that the eluates containing nucleic acids are opaque, indicating the presence of contaminations which may interfere with further usage of the isolated nucleic acids.

It was therefore an object of the present invention to provide a means which overcomes at least one of the abovementioned disadvantages of the prior art and in the process has lysis, binding and/or wash properties which are as good or better, if possible.

The object is achieved by a lysis, binding and/or wash reagent according to Claim 1 of the present invention. Accordingly, a lysis, binding and/or wash reagent is provided, comprising:
  at least one chaotropic compound,
  at least one buffer compound, preferably selected from the group comprising tris(hydroxymethyl)aminomethane (TRIS), N-(tri(hydroxymethyl)methyl)glycine (Tricine), N,N-bis(2-hydroxyethyl)glycine (BICINE), N-(2-hydroxyethyl)piperazine-N'-(2-ethanesulphonic acid) (HEPES), piperazine-1,4-bis(2-ethanesulphonic acid) (PIPES), N-cyclohexyl-2-aminoethanesulphonic acid (CHES), 2-(N-morpholino)ethanesulphonic acid (MES), 3-(N-morpholino)propanesulphonic acid (MOPS) and/or phosphate buffer, and
  at least one polyoxyethylene-based non-ionic surfactant selected from the group comprising polyoxyethylene fatty alcohol ether, polyoxyethylene alkylphenyl ether and/or polyoxyethylene-polyoxypropylene block copolymers in the range from ≥8% weight/volume to ≤50% weight/volume, based on the total volume of the reagent.

The term "lysis, binding and/or wash reagent" means for the purposes of the present invention reagents that are lysis reagents, binding reagents or wash reagents, and also reagents which may act as lysis reagent and also as binding reagent and also as wash reagent. More specifically, the term "lysis, binding and/or wash reagent" means for the purposes of the present invention also mixtures of lysis reagents, binding reagents and/or wash reagents of the invention.

The term "reagent" means for the purposes of the present invention lysis, binding and/or wash reagent.

The term "chaotropic compound" means for the purposes of the present invention compounds which act in a denaturing fashion on proteins and which in particular destroy the regular structure of liquid water, which is based on the formation of hydrogen bonds.

The term "buffer compound" means for the purposes of the present invention compounds which may provide buffering or pH stabilization of an aqueous solution.

The term "phosphate buffer" means for the purposes of the present invention phosphate salts such as dihydrogen phosphates, for example potassium dihydrogen phosphate ($KH_2PO_4$) or sodium dihydrogen phosphate ($NaH_2PO_4$), and hydrogen phosphates, for example disodium hydrogen phosphate dihydrate ($Na_2HPO_4.2H_2O$) or dipotassium hydrogen phosphate. Mixtures of the phosphate salts may likewise be used. Another common phosphate buffer is PBS (phosphate buffered saline) which contains sodium chloride, $Na_2HPO_4$, potassium chloride, and $KH_2PO_4$.

The term "nucleic acid" means for the purposes of the present invention—but is not limited to—natural, preferably isolated, linear, branched or circular nucleic acids such as RNA, in particular mRNA, siRNA, miRNA, snRNA, tRNA, hnRNA or ribozymes, DNA, plasmid DNA and the like, synthetic or modified nucleic acids, in vitro transcripts, for example oligonucleotides, more specifically primers, probes or standards useable for PCR, nucleic acids labelled with digoxygenin, biotin or fluorescent dyes, methylated nucleic acids or "PNAs" ("peptide nucleic acids").

The term "surfactant" means for the purposes of the present invention interface-active and/or surface-active substances.

The term "fatty alcohol" means for the purposes of the present invention alcohols having a chain length of from 6 to 22 carbon atoms, preferably 8 to 20 carbon atoms, preferentially 10 to 18 carbon atoms, particularly preferably 12 to 18 carbon atoms. Preference is in particular given to alcohols having 12, 14, 16 or 18 carbon atoms. Although the fatty alcohols may be mono- or polyunsaturated, they are preferably saturated fatty alcohols.

"Polyoxyethylene" means for the purposes of the present invention an $HO-(CH_2CH_2O)_n$ unit, with n being preferably an integer from 2 to 150, further preferably from 4 to 120, still further preferably from 8 to 80, and most preferably an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150.

"Polyoxypropylene" means for the purposes of the present invention an $HO-(CH_2CH_2CH_2O)_n$ unit, with n being preferably an integer from 10 to 90, further preferably from 20 to 80, still further preferably from 30 to 70, and most preferably n being an integer selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and 90.

The information "% weight/volume", "% (weight/volume)", or "% (w/v)" means for the purposes of the present invention the information of grams of surfactant per 100 ml of reagent or composition, for example.

Surprisingly, the lysis, binding and/or wash reagents of the invention were found to have improved stability during storage. Thus, for example, lysis, binding and/or wash reagents of the invention may have a stable pH during storage at room temperature for three, preferably six, months, further preferably at least eight months. More specifically, lysis, binding and/or wash reagents of the invention may also have a stable pH when stored at elevated temperatures, for example at 50° C., for several weeks, preferably for several months.

This has turned out to be advantageous for lysis, binding and/or wash reagents, since pH instability is suspected to be connected to the occurrence of contaminations in the eluate obtained after isolation, which contains the nucleic acids.

Polyoxyethylene-based non-ionic surfactants preferred according to the invention are polyoxyethylene fatty alcohol ethers.

Examples of suitable polyoxyethylene fatty alcohol ethers are polyethoxylated lauryl, cetyl, oleyl, or stearyl alcohols which may be used alone or as mixture.

According to a preferred embodiment of the invention, the polyoxyethylene fatty alcohol ether comprises a fatty alcohol component having from 6 to 22 carbon atoms and a polyoxyethylene component having from 2 to 150 $(CH_2CH_2O)$ units.

According to a particularly preferred embodiment of the invention, the polyoxyethylene fatty alcohol ether is selected from the group comprising polyoxyethylene lauryl ether, polyoxyethylene cetyl ether, polyoxyethylene stearyl ether, and/or polyoxyethylene oleyl ether.

Polyoxyethylene-based non-ionic surfactants, in particular polyoxyethylene fatty alcohol ethers, have turned out to be advantageous for a broad range of applications within the present invention. Improved stability during storage can be observed in particular with lysis, binding and/or wash reagents comprising buffer compounds preferably selected from the group comprising tris(hydroxymethyl)aminomethane (TRIS), N-(tri(hydroxymethyl)methyl)glycine (Tricine), N,N-bis(2-hydroxyethyl)glycine (BICINE), N-(2-hydroxyethyl)piperazine-N'-(2-ethanesulphonic acid) (HEPES), piperazine-1,4-bis(2-ethanesulphonic acid) (PIPES), N-cyclohexyl-2-aminoethanesulphonic acid (CHES), 2-(N-morpholino)ethanesulphonic acid (MES), 3-(N-morpholino)propanesulphonic acid (MOPS) and/or phosphate buffer.

The lysis, binding and/or wash reagents of the invention were found to have advantageous effects in particular with a content of polyoxyethylene-based non-ionic surfactant selected from the group comprising polyoxyethylene fatty alcohol ether, polyoxyethylene alkylphenyl ether, and/or polyoxyethylene-polyoxypropylene block copolymers in the range from ≥8% (weight/volume) to ≤50% (weight/volume), based on the total volume of the lysis, binding and/or wash reagent.

If mixtures of surfactants are used, the concentration information is preferably the total surfactant content, for example in the range from ≥8% (weight/volume) to ≤50% (weight/volume), based on the total volume of the reagent.

This has turned out to be advantageous in particular for lysis reagents within the present invention.

Preferred polyoxyethylene fatty alcohol ethers are ethoxylated lauryl, cetyl, oleyl or stearyl alcohols selected from the group comprising polyoxyethylene lauryl ether, polyoxyethylene cetyl ether, polyoxyethylene stearyl ether and/or polyoxyethylene oleyl ether.

Preferred polyoxyethylene fatty alcohol ethers are selected from the group comprising polyoxyethylene(4) lauryl ether, polyoxyethylene(23) lauryl ether, polyoxyethylene(2) cetyl ether, polyoxyethylene(10) cetyl ether, polyoxyethylene(20) cetyl ether, polyoxyethylene(2) stearyl ether, polyoxyethylene(10) stearyl ether, polyoxyethylene(20) stearyl ether, polyoxyethylene(2) oleyl ether, polyoxyethylene(10) oleyl ether, polyoxyethylene(20) oleyl ether and/or polyoxyethylene(100) stearyl ether. The numbers here indicate the average number of ethylene oxide units.

Particularly suitable according to the invention are polyoxyethylene fatty alcohol ethers sold under the trade name Brij®, for example by ICI Surfactants.

Examples of suitable polyoxyethylene lauryl, polyoxyethylene cetyl, polyoxyethylene oleyl or polyoxyethylene stearyl alcohol ethers are preferably selected from the group comprising polyoxyethylene(4) lauryl ether (Brij® 30), polyoxyethylene(23) lauryl ether (Brij® 35), polyoxyethylene(2) cetyl ether (Brij® 52), polyoxyethylene(10) cetyl ether (Brij® 56), polyoxyethylene(20) cetyl ether (Brij® 58), polyoxyethylene(2) stearyl ether (Brij® 72), polyoxyethylene(10) stearyl ether (Brij® 76), polyoxyethylene(20) stearyl ether (Brij® 78), polyoxyethylene(2) oleyl ether (Brij® 92), polyoxyethylene(10) oleyl ether (Brij® 97), polyoxyethylene(20) oleyl ether (Brij® 98) and/or polyoxyethylene(100) stearyl ether (Brij® 700).

Suitable polyoxyethylene lauryl, polyoxyethylene cetyl, polyoxyethylene oleyl or polyoxyethylene stearyl alcohol ethers may also be used as powders, for example polyoxyethylene(21) stearyl ether powder (Brij® 721P).

Another advantage of the lysis, binding and/or wash reagent of the invention may be provided by lysis, binding and/or wash reagents, when used for isolating and/or purifying nucleic acids, showing a consistently good yield of the isolated nucleic acids, even if the lysis, binding and/or wash reagent has been stored at room temperature or at elevated temperatures, for example up to 50° C., for several weeks or several months, while prior art buffers, in particular buffers containing Tween® 20, show lower yields of nucleic acids after storage.

A particular advantage of the use of lysis, binding and/or wash reagents of the invention is the fact that an eluate containing the nucleic acids is not or only slightly opaque, even after several weeks or several months of storage. It is therefore an advantage that the eluate may contain no or at least distinctly fewer contaminations, thereby rendering the further use of the eluate containing the nucleic acids substantially more advantageous because further time-consuming purification steps that reduce the yield of nucleic acids may be dispensed with.

Less preference is given to the lysis, binding and/or wash reagents comprising lauryl alcohol ethers of polyoxyethylene, for example polyoxyethylene(4) lauryl ether (Brij® 30) or polyoxyethylene(23) lauryl ether (Brij® 35). Therefore, in a preferred embodiment, the lysis, binding and/or wash reagents do not contain any of these substances. In a particularly preferred embodiment, the polyoxyethylene fatty alcohol ether of the lysis, binding and/or wash reagent is not polyoxyethylene lauryl ether.

In a preferred embodiment of the invention, the polyoxyethylene fatty alcohol ether is selected from the group comprising polyoxyethylene cetyl ether, polyoxyethylene stearyl ether and/or polyoxyethylene oleyl ether.

Preference is given to polyoxyethylene cetyl, polyoxyethylene oleyl, or polyoxyethylene stearyl alcohol ethers selected from the group comprising polyoxyethylene(10) cetyl ether (Brij® 56), polyoxyethylene(20) cetyl ether (Brij® 58), polyoxyethylene(20) stearyl ether (Brij® 78) and/or polyoxyethylene(20) oleyl ether (Brij® 98).

Particular preference is given to polyoxyethylene cetyl or polyoxyethylene oleyl alcohol ethers, preferably selected from the group comprising polyoxyethylene(10) cetyl ether (Brij® 56), polyoxyethylene(20) cetyl ether (Brij® 58) and/or polyoxyethylene(20) oleyl ether (Brij® 98).

More particularly, lysis, binding and/or wash reagents according to the invention comprising polyoxyethylene fatty alcohol ethers, in particular polyoxyethylene cetyl or polyoxyethylene oleyl alcohol ethers, by comparison stand out by a particularly good yield of isolated nucleic acids, in particular viral DNA. More specifically, both use of a freshly prepared lysis and/or binding reagent containing polyoxyethylene cetyl alcohol ether and use after several weeks, in particular several months, of storage at 50° C. for isolating DNA of Hepatitis B virus (HBV) were surprisingly found to produce a markedly increase yield of viral DNA in comparison with lysis buffers containing Tween® 20. This may provide in particular a particular advantage of the lysis and/or binding reagent of the invention because Hepatitis B virus (HBV) is known to be difficult to lyse. The lysis reagent of the invention is particularly suitable for isolating viral DNA.

Furthermore suitable are polyethoxylated lauryl, cetyl, stearyl or oleyl alcohols which are available, for example, under the INCI names laureth, ceteth, steareth or oleth.

Examples of furthermore suitable ethoxylated dodecyl, lauryl, cetyl, stearyl or oleyl alcohols are available under names selected from the group comprising laureth-9, laureth-4, laureth-23, ceteth-2, ceteth-20, steareth-2, steareth-10, steareth-20, oleth-2, oleth-10 and/or oleth-20.

Further preferred polyoxyethylene-based non-ionic surfactants are polyoxyethylene alkylphenyl ethers. Preference is given to polyoxyethylene alkylphenyl ethers having an alkyl group containing from five to 15 carbon atoms, preferably containing 6 to 10 carbon atoms. Further preference is given to branched or unbranched $C_7$- to $C_{10}$-alkyl groups, more particularly branched or unbranched $C_8$- and $C_9$-alkyl groups, particularly preferably isooctyl groups and nonyl groups.

In a preferred embodiment of the invention, the polyoxyethylene alkylphenyl ether is selected from the group comprising polyoxyethylene nonylphenyl ether and/or polyoxyethylene isooctylphenyl ether. Suitable polyoxyethylene nonylphenyl ethers and polyoxyethylene isooctylphenyl ethers are obtainable, for example, under the trade name Igepal®, for example from BASF.

Examples of suitable polyoxyethylene nonylphenyl ethers and polyoxyethylene isooctylphenyl ethers are preferably selected from the group comprising polyoxyethylene(2) nonylphenyl ether (Igepal® CO-210), polyoxyethylene(2) isooctylphenyl ether (Igepal® CA-210), polyoxyethylene(5) nonylphenyl ether (Igepal® CO-520), polyoxyethylene(5) isooctylphenyl ether (Igepal® CA-520), polyoxyethylene(9) nonylphenyl ether (Igepal® CO-630), polyoxyethylene(9) isooctylphenyl ether (Igepal® CA-630), polyoxyethylene (12) nonylphenyl ether (Igepal® CO-720), polyoxyethylene (12) isooctylphenyl ether (Igepal® CA-720) and/or polyoxyethylene(100) nonylphenyl ether (Igepal® CO-990).

Further preferred polyoxyethylene-based non-ionic surfactants are polyoxyethylene-polyoxypropylene block copolymers. Polyoxyethylene-polyoxypropylene block copolymers are also referred to as "poloxamers". Preference is given to polyoxyethylene-polyoxypropylene block copolymers of the empirical formula $HO(C_2H_4O)_a(C_3H_6O)_b(C_2H_4O)_aH$, where "a" refers to the number of polyoxyethylene units and "b" refers to the number of polyoxypropylene units, with the a/b weight ratio preferably being in the range from 0.1 to 3.

"a" is more particularly in the range from 2 to 150, preferably in the range from 4 to 120, further preferably in the range from 8 to 80, still further preferably "a" is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150, and most preferably "a" is an integer selected from 2, 4, 10, 20, 23, 40, 55, 70 and 100.

"b" is more particularly in the range from 10 to 90, preferably in the range from 20 to 80, further preferably in the range from 30 to 70, still further preferably "b" is an integer selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and 90, and most preferably "b" is an integer selected from 15, 18, 23, 40, 55, 67 and 75.

Further preference is given to polyoxyethylene-polyoxypropylene block copolymers having polyoxyethylene and polyoxypropylene blocks of different lengths, in which a polyoxypropylene block having from 15 to 67 polypropylene units is enclosed by two polyoxyethylene blocks having independently of one another in each case from 2 to 130 polyethylene units.

Suitable polyoxyethylene-polyoxypropylene block copolymers can be obtained, for example, under the trade name Pluronic® or Synperonic®, for example from BASF.

Examples of suitable polyoxyethylene-polyoxypropylene block copolymers are preferably selected from the group comprising Pluronic® PE 6200, Pluronic® PE 6400, Pluronic® PE 6800, Pluronic® PE 10300, Pluronic® PE 10500, Pluronic® F127, Pluronic® F108, Synperonic® F108, Synperonic® F127 and/or Synperonic® F68.

According to a preferred embodiment of the invention, the lysis, binding and/or wash reagent comprises a non-ionic surfactant in the range from ≥9% (weight/volume) to ≤40% (weight/volume), preferably in the range from ≥10% (weight/volume) to ≤30% (weight/volume), preferentially in the range from ≥15% (weight/volume) to ≤20% (weight/volume), based on the total volume of the reagent.

According to a preferred embodiment of the invention, the chaotropic compound is a sodium salt or guanidinium salt, preferably selected from the group comprising sodium iodide, sodium perchlorate, guanidinium hydrochloride, guanidinium thiocyanate, guanidinium isothiocyanate, and/or a mixture of two or more salts thereof. The chaotropic compound is preferably a guanidinium salt, preferentially selected from the group comprising guanidinium hydrochloride, guanidinium thiocyanate, and/or guanidinium isothiocyanate.

In particular, a combination of the abovementioned chaotropic compounds and the polyoxyethylene-based non-ionic surfactants has turned out to be advantageous for lysing virus cells and isolating nucleic acids from virus cells.

Suitable concentrations and amounts of chaotropic compounds may vary depending on the type of samples or parameters of lysis, with concentrations of the chaotropic compound in the range from ≥0.1 M to ≤10 M, based on the total volume of the reagent, being generally advantageous. Preference is given to the concentrations of the chaotropic compound of the lysis, binding and/or wash reagent being in the range from ≥0.5 M to ≤8 M, preferably in the range from ≥0.9 M to ≤6 M.

The concentrations of the chaotropic compound of the lysis reagent are preferably in the range from ≥3 M to ≤7 M, particularly preferably in the range from ≥4 M to ≤6 M. The concentrations of the chaotropic compound of the binding reagent are preferably in the range from ≥0.5 M to ≤7 M, particularly preferably in the range from ≥1 M to ≤6 M. The concentrations of the chaotropic compound of the wash reagent are preferably in the range from ≥0.5 M to ≤3.5 M, particularly preferably in the range from ≥0.9 M to ≤3 M.

According to another preferred embodiment, the lysis, binding and/or wash reagent comprises at least one buffer compound selected from the group comprising tris(hydroxymethyl)aminomethane (TRIS), N-(2-hydroxyethyl)piperazine-N'-(2-ethanesulphonic acid) (HEPES), 3-(N-morpholino)propanesulphonic acid (MOPS) and/or phosphate buffer.

According to a particularly preferred embodiment, the lysis, binding and/or wash reagent comprises at least one buffer compound selected from the group comprising tris(hydroxymethyl)aminomethane (TRIS) and/or N-(2-hydroxyethyl)piperazine-N'-(2-ethanesulphonic acid) (HEPES).

The lysis, binding and/or wash reagent is preferably an aqueous solution.

According to a further preferred embodiment, the lysis, binding and/or wash reagent has a pH in the range from ≥4 to ≤12, more particularly in the range from ≥6 to ≤11, preferably in the range from ≥7 to ≤10, particularly preferably in the range from ≥8 to ≤9.

In preferred embodiments, the lysis, binding and/or wash reagent, in particular the lysis reagent, may furthermore have enzymes, for example lytic enzymes, in particular, for example, proteinase K, protease (e.g. QIAGEN Protease), zymolase, lyticase, achromopeptidase, lysostaphin, lysozyme and, depending on use, nucleases, for example DNase and/or RNase.

Lysis, binding and/or wash reagents of the invention may be lysis reagents, binding reagents or wash reagents, or mixtures of lysis reagents, binding reagents and/or wash reagents of the invention.

Nucleic acids are immobilized on a matrix based on one or more silicon oxide compounds in the presence of a chaotropic compound preferentially in the presence of a branched or unbranched alkanol. Preference is therefore given to the binding reagent comprising at least one branched or unbranched alkanol.

Preferably useable are short-chain branched or unbranched alkanols having from one to five carbon atoms. According to a preferred embodiment of the invention, the branched or unbranched alkanol is an alcohol having from one to five carbon atoms, preferably selected from the group comprising methanol, ethanol, isopropanol, n-propanol, branched or unbranched butanol or pentanol, and/or mixtures thereof.

Unless described otherwise, the definitions "branched or unbranched alkanol", in particular propanol, butanol and pentanol comprise any consumable isomeric forms of the particular radicals. Thus, for example, branched or unbranched propanol comprises n-propanol and isopropanol, branched or unbranched butanol comprises isobutanol, sec-butanol and tert-butanol, and branched or unbranched pentanol comprises, for example, n-pentanol and isopentanol. Preference is given to using alcohols selected from the group comprising methanol, ethanol, isopropanol and/or mixtures thereof, and particular preference is given to using alcohols selected from the group comprising ethanol, isopropanol, and/or mixtures thereof.

According to a preferred embodiment of the invention, the binding reagent comprises branched or unbranched alkanol in the range from ≥20% by volume to ≤80% by volume, preferentially in the range from ≥40% by volume to ≤70% by volume, preferably in the range from ≥50% by volume to ≤60% by volume, based on the total volume of the binding reagent.

When volume and/or weight contents are specified, it is self-evident to a person skilled in the art that said volume and/or weight contents of the individual components are chosen in such a way that the total volume or total weight of the components does not exceed 100% by volume or 100% by weight.

The present invention moreover relates to the use of a lysis, binding and/or wash reagent of the invention for isolating and/or purifying nucleic acids.

The present invention furthermore relates to a method for isolating and/or purifying nucleic acids from a nucleic acid-containing biological sample, comprising the following method steps:
a) lysing the biological sample,
b) immobilizing the released nucleic acid(s) on a matrix based on one or more silicon oxide compound(s) in the presence of a chaotropic compound and/or a branched or unbranched alkanol,
c) optionally washing the nucleic acid(s) immobilized on the matrix,
d) optionally removing the bound nucleic acid,
wherein lysing and/or immobilizing are carried out in the presence of a lysis and/or binding composition comprising:
at least one chaotropic compound, and
at least one polyoxyethylene-based non-ionic surfactant selected from the group comprising polyoxyethylene fatty alcohol ether, polyoxyethylene alkylphenyl ether and/or polyoxyethylene-polyoxypropylene block copolymers in the range from ≥0.1% weight/volume to ≤50% weight/volume, based on the total volume of the composition.

The term "composition" means for the purposes of the present invention lysis and/or binding composition.

In preferred embodiments of the method, a lysis reagent of the invention is used for lysing the sample. The lysis reagent is brought into contact with the biological sample to be lysed. One or more enzymes may be added independently of one another at various time points, depending on the use. The sample may be in liquid form, for example in the case of liquid clinical samples. Clinical samples which contain solid components, such as stool samples or swab samples, are usually suspended in suitable aqueous solutions prior to further analysis. Cell cultures are usually removed from the culture medium before lysis, but drying the sample completely is avoided in most cases. In the case of completely dried samples, for example lyophilizates, the sample is reconstituted in aqueous solutions prior to further processing, for example lyophilizates of virus standards. The samples to be lysed therefore usually contain some liquid. This liquid present in the sample is brought into contact with the lysis reagent. In this respect, a method for isolating and/or purifying nucleic acids from a sample usually involves a lysis composition which contains lysis reagent and other liquid of the sample or of solutions already added to said sample.

The term "lysis and/or binding composition" refers for the purposes of the present invention to a lysis and/or binding reagent which is used in a method for isolating and/or purifying nucleic acids from a sample and which may contain further liquid in addition to lysis, binding and/or wash reagent. The lysis and/or binding composition may preferably comprise lysis and/or binding reagent of the invention.

According to a further preferred embodiment of the method, the released nucleic acid is immobilized on a matrix based on one or more silicon oxide compound in the presence of a binding composition of the invention.

Preference is given to contacting the lysis and/or binding reagent of the invention with the lysed sample. The lysis composition or another solution in which lysis was carried out may be removed before the sample is brought into contact with the binding reagent. Preference is given to not removing the lysis composition. Preferably, a binding reagent is brought into contact with a sample comprising lysis composition.

According to a particularly preferred embodiment of the method, lysing is carried out in the presence of a lysis composition and immobilizing is carried out in the presence of a binding composition. Accordingly, immobilizing is preferably carried out in the presence of a mixture of a lysis composition and binding composition.

Optionally, the lysis reagent may also be employed as binding reagent at the same time. Further optionally, the binding reagent may also be employed as lysis reagent. Also optionally, the binding reagent may also be employed as wash reagent.

The lysis and/or binding composition comprises at least one chaotropic compound and at least one polyoxyethylene-based non-ionic surfactant selected from the group comprising polyoxyethylene fatty alcohol ether, polyoxyethylene alkylphenyl ether and/or polyoxyethylene-polyoxypropylene block copolymers in the range from ≥0.1% (weight/volume) to ≤50% (weight/volume), based on the total volume of the composition. If mixtures of surfactants are used, preferably the total surfactant content is, for example, in the range from ≥0.1% (weight/volume) to ≤50% (weight/volume) in total, based on the total volume of the composition.

The advantage of such a method for isolating and/or purifying nucleic acids from a nucleic acid-containing biological sample, for example, is that of an eluate containing the nucleic acids being not or only slightly opaque, even after several weeks or several months of storage at room temperature or elevated temperatures, for example, 50° C., when a lysis and/or binding composition comprising at least one chaotropic compound and at least one polyoxyethylene-based non-ionic surfactant selected from the group comprising polyoxyethylene fatty alcohol ether, polyoxyethylene alkylphenyl ether and/or polyoxyethylene-polyoxypropylene block copolymers in the range from ≥0.1% (weight/volume) to ≤50% (weight/volume), based on the total volume of the composition, is used. Therefore, advantageously, the eluate may contain no or at least distinctly fewer contaminations. This renders further use of the eluate containing the nucleic acids substantially more advantageous, because further time-consuming purification steps that reduce the yield of nucleic acids may be dispensed with.

Another advantage of such a method for isolating and/or purifying nucleic acids from a nucleic acid-containing biological sample, for example, is that of making possible a particularly good yield of isolated nucleic acids, in particular viral DNA, for example the DNA of Hepatitis B virus (HBV).

A "biological sample" may be understood as meaning a material on a particulate or molecular basis, in particular viruses, phages and cells such as bacterial cells, yeast or mould cells or human, animal or plant cells. The method is particularly suitable for isolating nucleic acids such as DNA or RNA from sample materials of human or animal origin, for example clinical samples such as blood, plasma, serum, mouth, throat and nose rinses, bronchoalveolar lavages, urine, cerebral fluid, sputum, saliva, stool, aspirates, smears/swabs such as, for example, nasal smears/swabs, buccal smears/swabs, cervical smears/swabs, vaginal smears/swabs, urethral smears/swabs, pharyngeal smears/swabs, perineal smears/swabs, and rectal smears/swabs, stool, aspirates, epithelial smears/swabs, biopsies, and other tissue or bone marrow samples, and also cultures of these sample materials in suitable nutrient media.

The sample can also be from the field of environmental analysis, food analysis, or molecular biological research, for example from bacterial cultures, yeast or fungal cultures, viral cultures, phage lysates or products of amplification processes, for example of a polymerase chain reaction (PCR).

The method of the invention is preferably suitable for isolating and/or purifying genomic DNA, mitochondrial DNA, plasmid DNA, viral DNA and viral RNA, and for isolating and purifying intracellular RNA from whole blood, for example for reverse transcription polymerase chain reaction (RT-PCR), and also for isolating and/or purifying freely circulating nucleic acids present in cell-free sample materials. The method of the invention is particularly suitable for isolating and/or purifying viral DNA.

The biological sample is lysed in step a) of the method. In principle, the methods listed below, selected from the group comprising lysis with the aid of ionic and non-ionogenic surfactants, for example sodium dodecyl sulphate (SDS), lithium dodecyl sulphate (LiDS) or sodium lauroyl sarcosinate (sarkosyl) in suitable reagents or buffers, the use of chaotropic salts, mechanical tearing apart, for example by means of ultrasound, a "French press", grinding with particles such as glass balls, ceramic balls or metal particles, or in liquid nitrogen, by repeated cycles of freezing and thawing, or by boiling, enzymatic lysis, lysis by freeze-drying, lysis by osmotic shock, microwave and/or temperature treatment, and/or combinations thereof, are suitable for lysing a biological sample. Lysis is preferably carried out in the presence of chaotropic salts. Preference is given to lysing the biological sample in the presence of a lysis composition comprising at least one chaotropic compound and at least one polyoxyethylene-based non-ionic surfactant selected from the group comprising polyoxyethylene fatty alcohol ether, polyoxyethylene alkylphenyl ether and/or polyoxyethylene-polyoxypropylene block copolymers in the range from ≥0.1% (weight/volume) to ≤50% (weight/volume), based on the total volume of the lysis composition.

More specifically, a combination of chaotropic agents and polyoxyethylene-based non-ionic surfactant selected from the group comprising polyoxyethylene fatty alcohol ether, polyoxyethylene alkylphenyl ether, and/or polyoxyethylene-polyoxypropylene block copolymers is particularly effective in the lysis of virus cells.

The lysis and/or binding composition comprises at least one chaotropic compound and at least one polyoxyethylene-based non-ionic surfactant selected from the group comprising polyoxyethylene fatty alcohol ether, polyoxyethylene alkylphenyl ether, and/or polyoxyethylene-polyoxypropylene block copolymers.

Reference is made here to the entire contents of the description above in respect of polyoxyethylene-based non-ionic surfactants.

Examples of suitable ethoxylated fatty alcohols are ethoxylated dodecyl, lauryl, cetyl, oleyl or stearyl alcohols which may be used alone or as a mixture. Preferred polyoxyethylene fatty alcohol ethers are ethoxylated lauryl, cetyl, oleyl or stearyl alcohols selected from the group comprising polyoxyethylene lauryl ether, polyoxyethylene cetyl ether, polyoxyethylene stearyl ether, and/or polyoxyethylene oleyl ether.

Preferred polyoxyethylene fatty alcohol ethers are selected from the group comprising polyoxyethylene(4) lauryl ether, polyoxyethylene(23) lauryl ether, polyoxyethylene(2) cetyl ether, polyoxyethylene(10) cetyl ether, polyoxyethylene(20) cetyl ether, polyoxyethylene(2) stearyl ether, polyoxyethylene(10) stearyl ether, polyoxyethylene(20) stearyl ether, polyoxyethylene(2) oleyl ether, polyoxyethylene(10) oleyl ether, polyoxyethylene(20) oleyl ether, and/or polyoxyethylene(100) stearyl ether. The numbers here indicate the average number of ethylene oxide units.

Examples of suitable polyoxyethylene lauryl, polyoxyethylene cetyl, polyoxyethylene oleyl, or polyoxyethylene stearyl alcohol ethers are preferably selected from the group comprising polyoxyethylene(4) lauryl ether (Brij® 30) or polyoxyethylene(23) lauryl ether (Brij® 35), polyoxyethylene(2) cetyl ether (Brij® 52), polyoxyethylene(10) cetyl ether (Brij® 56), polyoxyethylene(20) cetyl ether (Brij® 58), polyoxyethylene(2) stearyl ether (Brij® 72), polyoxyethylene(10) stearyl ether (Brij® 76), polyoxyethylene(20) stearyl ether (Brij® 78), polyoxyethylene(2) oleyl ether (Brij® 92), polyoxyethylene(10) oleyl ether (Brij® 97), polyoxyethylene(20) oleyl ether (Brij® 98), and/or polyoxyethylene(100) stearyl ether (Brij® 700).

According to a preferred embodiment of the invention, the polyoxyethylene fatty alcohol ether comprises a fatty alcohol component having from 6 to 22 carbon atoms and a polyoxyethylene component containing from 2 to 150 ($CH_2CH_2O$) units.

In a particularly preferred embodiment of the method, the polyoxyethylene fatty alcohol ether is selected from the group comprising polyoxyethylene lauryl ether, polyoxyethylene cetyl ether, polyoxyethylene stearyl ether, and/or polyoxyethylene oleyl ether.

In a preferred embodiment of the method, the polyoxyethylene fatty alcohol ether is selected from the group comprising polyoxyethylene cetyl ether, polyoxyethylene stearyl ether and/or polyoxyethylene oleyl ether. In this embodiment, less preference is given to the lysis and/or binding composition comprising lauryl alcohol ethers of polyoxyethylene, for example polyoxyethylene(4) lauryl ether (Brij® 30) or polyoxyethylene(23) lauryl ether (Brij® 35). Preference is therefore given to the lysis and/or binding composition not containing any of these substances. In a particularly preferred embodiment, the polyoxyethylene fatty alcohol ether of the lysis and/or binding composition is not polyoxyethylene lauryl ether.

Preference is given to polyoxyethylene cetyl, polyoxyethylene oleyl, or polyoxyethylene stearyl alcohol ether, preferably selected from the group comprising polyoxyethylene(10) cetyl ether (Brij® 56), polyoxyethylene(20) cetyl ether (Brij® 58), polyoxyethylene(20) stearyl ether (Brij® 78) and/or polyoxyethylene(20) oleyl ether (Brij® 98). Particular preference is given to polyoxyethylene cetyl or polyoxyethylene oleyl alcohol ethers, preferably selected from the group comprising polyoxyethylene(10) cetyl ether (Brij® 56), polyoxyethylene(20) cetyl ether (Brij® 58) and/or polyoxyethylene(20) oleyl ether (Brij® 98).

Furthermore suitable are polyethoxylated lauryl, cetyl, stearyl or oleyl alcohols which are available, for example, under the INCI names laureth, ceteth, steareth or oleth.

Further preferred polyoxyethylene-based non-ionic surfactants are polyoxyethylene alkylphenyl ethers. Preference is given to polyoxyethylene alkylphenyl ethers having an alkyl group containing from five to 15 carbon atoms, preferably containing 6 to 10 carbon atoms. Further preference is given to branched or unbranched $C_7$- to $C_{10}$-alkyl groups, more particularly branched or unbranched $C_8$- and $C_9$-alkyl groups, particularly preferably isooctyl groups and nonyl groups. In a preferred embodiment of the method, the polyoxyethylene alkylphenyl ether is selected from the group comprising polyoxyethylene nonylphenyl ether and/or polyoxyethylene isooctylphenyl ether. Suitable polyoxyethylene nonylphenyl ethers and polyoxyethylene isooctylphenyl ethers are obtainable, for example, under the trade name Igepal®, for example from BASF.

Further preferred polyoxyethylene-based non-ionic surfactants are polyoxyethylene-polyoxypropylene block copolymers. Polyoxyethylene-polyoxypropylene block copolymers are also referred to as "poloxamers". Preference is given to polyoxyethylene-polyoxypropylene block copolymers of the empirical formula $HO(C_2H_4O)_a(C_3H_6O)_b(C_2H_4O)_aH$, where "a" refers to the number of polyoxyethylene units and "b" refers to the number of polyoxypropylene units, with the a/b weight ratio preferably being in the range from 0.1 to 3.

"a" is more particularly in the range from 2 to 150, preferably from 4 to 120, further preferably from 8 to 80, still further preferably "a" is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150, and most preferably "a" is an integer selected from 2, 4, 10, 20, 23, 40, 55, 70 and 100.

"b" is more particularly in the range from 10 to 90, preferably in the range from 20 to 80, further preferably in the range from 30 to 70, still further preferably "b" is an integer selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and 90, and most preferably "b" is an integer selected from 15, 18, 23, 40, 55, 67 and 75.

Further preference is given to polyoxyethylene-polyoxypropylene block copolymers having polyoxyethylene and polyoxypropylene blocks of different lengths, in which a polyoxypropylene block having from 15 to 67 polypropylene units is enclosed by two polyoxyethylene blocks having independently of one another in each case from 2 to 130 poly ethylene units.

Suitable polyoxyethylene-polyoxypropylene block copolymers can be obtained, for example, under the trade name Pluronic® or Synperonic®, for example from BASF.

According to a preferred embodiment of the method, the lysis and/or binding composition comprises a non-ionic surfactant in the range from ≥0.2% (weight/volume) to ≤30% (weight/volume), preferably in the range from ≥3% (weight/volume) to ≤10% (weight/volume), preferentially in the range from ≥3.2% (weight/volume) to ≤8% (weight/volume), based on the total volume of the composition.

This has turned out to be particularly advantageous for lysis compositions and for mixtures of lysis and binding compositions.

According to a preferred embodiment of the method, the chaotropic compound of the lysis and/or binding composition is a sodium salt or guanidinium salt, preferably selected from the group comprising sodium iodide, sodium perchlorate, guanidinium hydrochloride, guanidinium thiocyanate, guanidinium isothiocyanate, and/or a mixture of two or more salts thereof. The chaotropic compound is preferably a guanidinium salt, preferentially selected from the group comprising guanidinium hydrochloride, guanidinium thiocyanate, and/or guanidinium isothiocyanate.

In particular, a combination of the abovementioned chaotropic compounds and the polyoxyethylene-based non-ionic surfactants has turned out to be advantageous for lysing virus cells and isolating nucleic acids from virus cells.

Concentrations of the chaotropic compound of the lysis and/or binding composition in the range from ≥0.1 M to ≤10 M have turned out to be advantageous. Preference is given to the concentrations of the chaotropic compound in the range from ≥1 M to ≤8 M, preferably in the range from ≥3 M to ≤7 M, particularly preferably in the range from ≥4 M to ≤6 M.

According to a preferred embodiment of the method, the lysis and/or binding composition comprises at least one buffer compound selected from the group comprising tris (hydroxymethyl)aminomethane (TRIS), N-(tri(hydroxymethyl)methyl)glycine (Tricine), N,N-bis(2-hydroxyethyl) glycine (BICINE), N-(2-hydroxyethyl)piperazine-N'-(2-ethanesulphonic acid) (HEPES), piperazine-1,4-bis(2-ethanesulphonic acid) (PIPES), N-cyclohexyl-2-aminoethanesulphonic acid (CHES), 2-(N-morpholino) ethanesulphonic acid (MES), 3-(N-morpholino) propanesulphonic acid (MOPS) and/or phosphate buffer.

According to a further preferred embodiment of the method, the lysis and/or binding composition comprises at least one buffer compound selected from the group comprising tris(hydroxymethyl)aminomethane (TRIS), N-(2-hydroxyethyl)piperazine-N'-(2-ethanesulphonic acid) (HEPES) and/or phosphate buffer. According to a still further preferred embodiment of the method, the lysis and/or binding composition comprises at least one buffer compound selected from the group comprising tris(hydroxymethyl)aminomethane (TRIS) and/or N-(2-hydroxyethyl)piperazine-N'-(2-ethanesulphonic acid) (HEPES).

The biological sample may be lysed at room temperature, for example at 15° C. to 25° C., or at an elevated temperature, for example at temperatures in the range from ≥37° C. to ≤75° C.

In preferred embodiments, the lysis composition may furthermore have enzymes, for example proteinase K, protease (e.g. QIAGEN Protease), zymolase, lyticase, achromopeptidase, lysostaphin, lysozyme and, depending on use, nucleases, for example DNase and/or RNase.

The released nucleic acid(s) is(are) immobilized on a matrix based on one or more silicon oxide compound in the presence of a chaotropic compound and/or a branched or unbranched alkanol.

Preference is given to the binding composition comprising a branched or unbranched alkanol. According to a preferred embodiment, the branched or unbranched alkanol is an alcohol having from one to five carbon atoms, preferably selected from the group comprising methanol, ethanol, isopropanol, n-propanol, n-butanol, isobutanol, sec-butanol, tert-butanol, n-pentanol, isopentanol, and/or mixtures thereof.

According to a preferred embodiment, the binding composition comprises branched or unbranched alkanol in the range from ≥1% by volume to ≤80% by volume, preferentially in the range from ≥5% by volume to ≤70% by volume, preferably in the range from ≥10% by volume to ≤60% by volume, further preferably in the range from ≥15% by volume to ≤50% by volume, based on the total volume of the binding composition.

According to a preferred embodiment of the invention, a mixture of the binding composition comprises the lysis reagent and optionally one or more further additives, preferably branched or unbranched alkanol in the range from ≥1% by volume to ≤80% by volume, preferentially in the range from ≥5% by volume to ≤70% by volume, preferably in the range from ≥15% by volume to ≤50% by volume, based on the total volume of the mixture.

The nucleic acids are isolated by contacting the sample with a matrix based on one or more silicon oxide compounds such as silicon dioxide (silica), silicate, glass and/or silica gel and incubating it long enough for binding. The matrix may be in the usual designs known from the prior art, such as, for example, in the form of particles, as membrane or filter. To facilitate their removal, preference is given to the particles having magnetic properties. Incubation times between 10 seconds and 30 minutes may be convenient for nucleic acids. Incubation times in a range from 1 minute to 20 minutes, in particular of approx. 10 minutes, have turned out to be advantageous.

Nucleic acids are isolated preferably by using magnetic particles having a gelatinous silica coating. Nucleic acids are isolated preferably by using magnetic particles having a gelatinous silica coating and having an average particle size in the range from ≥1 µm to ≤25 µm, preferentially in the range from ≥5 µm to ≤15 µm and particularly preferably in the range from ≥6 µm to ≤10 µm, preferentially with a narrow size distribution. Further preferably, nucleic acids are isolated by using magnetic particles having a gelatinous silica coating and having an average particle size in the range from ≥1 µm to ≥5 µm, preferably with a narrow size distribution.

In a further preferred embodiment, the magnetic or magnetically attractable particles are particles having a magnetic core based on iron oxide, preferably selected from the group comprising magnetite ($Fe_3O_4$), maghemite ($\gamma$-$Fe_2$—$O_3$) and/or ferrites.

Magnetic silica particles which may be used in an advantageous manner are described, for example, in the international application WO 01/71732, the entire contents of which are hereby incorporated by reference.

In a preferred embodiment, a matrix based on one or more silicon oxide compound in the form of magnetic or magnetically attractable particles having a silica surface may be used.

Preference is given to carrying out binding at temperatures in the range from ≥15° C. to ≤75° C., preferably in the range from ≥20° C. to ≤70° C., particularly preferably in the range from ≥46° C. to ≤65° C., most preferably from ≥50° C. to ≤60° C. Binding may also be carried out at room temperature, for example at from ≥15° C. to ≤28° C.

After incubation, the nucleic acids bound to the matrix based on one or more silicon oxide compound are removed from the lysis and/or binding composition. When using magnetic silica particles, this may be achieved with the aid of a magnetic field. For example, the magnetic particles may be drawn to the wall of the vessel in which incubation had been carried out, collected in suitable pipette tips by applying a magnetic field, or immobilized on magnetic rods protected by plastic coatings. Examples of suitable method steps for removing the lysis and/or binding composition are removing by pipetting or aspirating the liquid or lifting the magnetic particles out in pipette tips or on magnetic rods, or lowering the lysis and/or binding mix, with the separated magnetic particles remaining at the same level.

Optionally, the nucleic acid(s) immobilized on the matrix may be washed prior to removal. The wash step is preferably carried out by incubating a wash solution with the loaded particles, involving preferably resuspension of said particles, for example by shaking or applying a magnetic field. The contaminated wash solution is preferably removed, as is the lysis and/or binding composition remaining after binding, in particular a mixture of lysis composition and/or binding composition.

The wash reagent used may be a conventional wash buffer or any other suitable medium. Generally, preference is given to wash reagents having a low to moderate ionic strength, for example a solution of 10 mM tris(hydroxymethyl)aminomethane (TRIS). Furthermore useable are wash buffers having relatively high salt concentrations, for example a solution of 4-6 M guanidinium hydrochloride. The wash reagents of the invention, described above, are likewise suitable wash reagents.

Furthermore, alcohol-containing wash reagents may also be used, for example aqueous solutions of alcohols having from one to five carbon atoms, preferably aqueous solutions of ethanol, in particular aqueous solutions of 50-100 percent strength ethanol.

Preference is given to washing the nucleic acid(s) immobilized on the matrix several times, for example 2 to 4 times, preferably with different wash reagents. In preferred embodiments, washing is carried out first with wash reagents having a low to moderate ionic strength and then with an aqueous, 70-100 percent strength solution of ethanol.

More specifically, using magnetic particles enables separation and/or wash steps to be carried out easily due to magnetic aggregation of the particles.

The last wash step or a water rinse may be followed by a step of drying the preferably magnetic particles, for example in vacuo or by evaporating the liquid or by letting the liquid evaporate.

According to step d) of the method, the bound nucleic acids may be removed from the matrix. Removing the nucleic acids is also referred to us eluting.

Preference may also be given to using the nucleic acids bound to the matrix, in particular to magnetic particles, without a removal step, for example for PCR or other amplification methods, DNA detection methods or DNA identification methods.

The bound nucleic acid may be removed from the particles by means of an elution reagent having a low salt content. More specifically, reagents having a salt content of less than 0.1 mol/l may be used as the elution reagent having a low salt content. Particular preference is given to the elution reagent containing the buffer compound tris(hydroxymethyl)aminomethane (TRIS). Particularly suitable for elution is furthermore demineralized water, optionally containing one or more additives, for example complexing agents such as ethylenediamine tetraacetate (EDTA), azide and/or buffer compounds, for example tris(hydroxymethyl) aminomethane (TRIS).

Using the lysis and/or binding composition, in particular, results in a particularly advantageous method for isolating nucleic acids from biological samples, in particular for isolating viral DNA.

Advantages arise in particular from the achievable good yields, even after storage of the lysis and/or binding reagents.

The present invention furthermore relates to a kit for isolating and/or purifying nucleic acids from a nucleic acid-containing biological sample, comprising a lysis, binding and/or wash reagent of the invention.

In preferred embodiments, the kit may furthermore contain a matrix based on one or more silicon oxide compound, in particular a matrix based on one or more silicon oxide compound in the form of magnetic or magnetically attractable particles having a silica surface. Examples of magnetic silica particles preferably contained in said kit are described in the international application WO 01/71732, the entire contents of which are hereby incorporated by reference.

In a further preferred embodiment, the kit may furthermore contain suitable wash and/or elution reagents, in particular the wash reagent according to the invention.

In another preferred embodiment, the kit may contain silanized support materials other than magnetic silica particles, preferably centrifugal columns with silica membranes.

The present invention furthermore relates to the use of polyoxyethylene-based non-ionic surfactants selected from the group comprising polyoxyethylene fatty alcohol ether, polyoxyethylene alkylphenyl ether, and/or polyoxyethylene-polyoxypropylene block copolymers, in particular polyoxyethylene fatty alcohol ethers selected from the group comprising polyoxyethylene lauryl ether, polyoxyethylene cetyl ether, polyoxyethylene stearyl ether and/or polyoxyethylene oleyl ether, for solubilizing lipids of a biological sample.

The term "lipid" means for the purposes of the present invention water-insoluble or at least mostly water-insoluble natural substances. The term "lipid" comprises for the purposes of the present invention fatty acids, the group of triglycerides comprising fats and oils, waxes, phospholipids, sphingolipids, liposaccharides, and the group of isoprenoids comprising steroids and carotenoids. More specifically, the term "lipid" means lipid components or structural components of the cell membranes of organisms, such as phospholipids and sphingolipids.

Preference is given to using polyoxyethylene-based non-ionic surfactants selected from the group comprising polyoxyethylene fatty alcohol ether, polyoxyethylene alkylphenyl ether, and/or polyoxyethylene-polyoxypropylene block copolymers for solubilizing lipids of a biological sample in methods for isolating and/or purifying nucleic acids from a nucleic acid-containing biological sample.

Reference is made here to the entire description above in respect of the polyoxyethylene-based non-ionic surfactants.

Particular preference is given to using polyoxyethylene fatty alcohol ethers selected from the group comprising polyoxyethylene lauryl ether, polyoxyethylene cetyl ether, polyoxyethylene stearyl ether, and/or polyoxyethylene oleyl ether for solubilizing lipids of a biological sample in methods for isolating and/or purifying nucleic acids from a nucleic acid-containing biological sample.

Particular preference is given to using the polyoxyethylene-based non-ionic surfactants, in particular polyoxyethylene fatty alcohol ethers, for solubilizing lipids of a biological sample in methods for isolating and/or purifying nucleic acids using a matrix based on one or more silicon oxide compound, preferably in the form of magnetic or magnetically attractable particles having a silica surface.

Advantageously, the eluate was found to contain no or at least markedly fewer contaminations when using the polyoxyethylene-based non-ionic surfactants, in particular polyoxyethylene fatty alcohol ethers, in methods for isolating and/or purifying nucleic acids using a matrix based on one or more silicon oxide compound, preferably in the form of magnetic or magnetically attractable particles having a silica surface.

In addition, the invention concerns the use of polyoxyethylene-based non-ionic surfactants selected from the group comprising polyoxyethylene fatty alcohol ether, polyoxyethylene alkylphenyl ether, and/or polyoxyethylene-polyoxypropylene block copolymers, preferably polyoxyethylene fatty alcohol ether selected from the group comprising polyoxyethylene lauryl ether, polyoxyethylene cetyl ether, polyoxyethylene stearyl ether and/or polyoxyethylene oleyl ether, for preparing storage-stable binding, lysis and/or wash reagents.

Reference is made here to the entire description above in respect of the polyoxyethylene-based non-ionic surfactants.

"Storage stable" here preferably means for the purposes of the invention that the properties of the lysis, binding or wash reagent that are relevant for the particular use, do not change during storage over a period of three months, preferably of 6 months, further preferably of at least 8 months, in such a way that this substantially impairs said use. In a preferred embodiment, storage stability is displayed at room temperature, further preferably also at an elevated storage temperature of 50° C., for example.

The pH has turned out to be one of the properties of the reagents that are relevant to the use. Preferentially, therefore, the former does not substantially change during storage of the reagents, with the pH preferably decreasing by less than 1 during storage of the reagents.

Further details, features and advantages of the subject of the invention can be found in the dependent claims and in the description hereinbelow of the accompanying figures and examples which illustrate by way of example exemplary embodiments of the present invention.

BRIEF DESCRIPTION OF THE DRAWINGS

(FIG. 1A) and 50° C. (FIG. 1).

The invention will be illustrated below likewise on the basis of examples. It will be appreciated that the latter shall be considered merely by way of illustration and shall not limit the present invention.

EXAMPLE 1: STABILITY TEST

A lysis reagent A containing 20% (w/v) Tween® 20 (Fluka), guanidinium isothiocyanate and tris(hydroxymethyl)aminomethane and lysis reagent B in which Tween® 20 had been replaced with 20% (w/v) Brij® 58 (Sigma) were freshly prepared in double-distilled water and each stored in sealed vessels at 25° C. and 50° C. for 33 weeks.

The pH of each solution was determined here with the aid of a pH meter (Metrohm) at temperatures in the range from 20° C. to 28° C. at the start of storage and at weekly intervals.

Figure 1A:
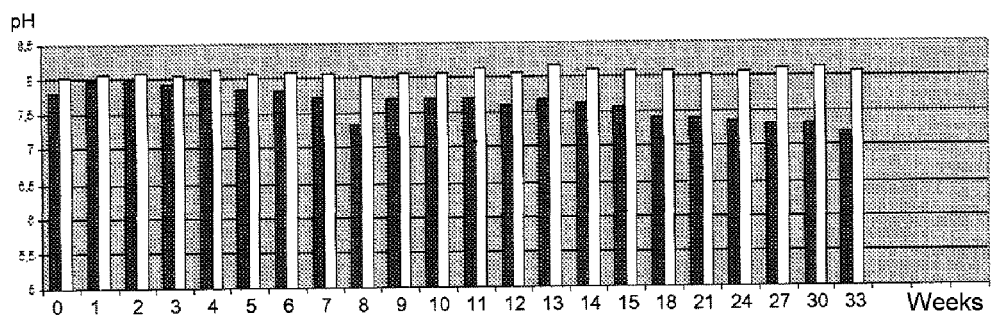
FIGS. 1A-1B depict the change in pH of the lysis reagent B of the invention, depicted as empty bars, and of the Tween 20®-containing lysis reagent A, depicted as filled bars, during 33 weeks of storage at 25° C.
Figure 1B:
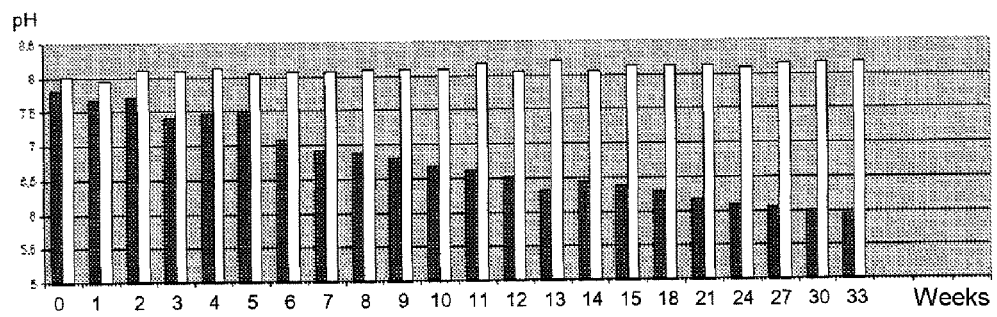

The bar chart depicted in FIG. 1A indicates that the pH of lysis reagent A decreased slightly from approx. pH 7.8 to pH 7.2 during 33 weeks of storage at 25° C., while the pH decreased from approx. pH 7.8 to approx. pH 5.9 during 33 weeks of storage at 50° C., as depicted in FIG. 1B. In contrast, the pH of lysis reagent B remained stable at approx. pH 8 during 33 weeks of storage at 25° C. and 50° C.

EXAMPLE 2: EXTRACTION OF VIRAL DNA

Negative, i.e. HBV virus-free, human plasma was admixed with $10^4$ sgU/ml hepatitis B virus (HBV). The viral DNA was extracted from in each case 1000 µl of the plasma sample, using the commercially available automation platform QIAsymphony® (Qiagen), by means of the automated protocol for purifying viral nucleic acids from plasma samples.

According to the protocol used, the sample was exposed to the protocol-defined volumes—of lysis reagent B containing guanidinium isothiocyanate, tris(hydroxy-methyl) aminomethane and 20% (w/v) Brij® 58 (Sigma) and proteinase K, and solution AVE containing carrier RNA. This was followed by incubation at 65° C. to lyse the sample. To the sample mix was then added the protocol-defined volume of binding reagent C containing guanidinium isothiocyanate, tris(hydroxymethyl)aminomethane and 9% (w/v) Brij® 58 (Sigma), and isopropanol. After a further 3 minutes of incubation, MagAttract suspension which contained the magnetic silicon dioxide particles was added and mixed, as specified in the protocol. During this time, the nucleic acids bind to the silicon oxide particles. The magnetic silicon oxide particles were then separated and the liquid phase was removed. To the silicon oxide particles was then added the protocol-defined volume of wash solution containing guanidinium thiocyanate and ethanol, and the particles were suspended in the wash solution. The supernatant was again removed and a protocol-defined volume of wash solution containing Tris, NaCl and ethanol was added and a second wash step was carried out. After separating and removing the liquid phase, the particles were washed with protocol-defined volumes of aqueous 80% strength ethanol. After separating the particles, the supernatant was removed, and the particles were dried in air for 8 minutes. To elute the DNA, protocol-defined volumes of eluting solution E were added, with the particles being suspended therein for 3 minutes. The particles were then removed, and the eluate was obtained.

According to said protocol, viral DNA was extracted from a further 1000 µl of plasma sample, with the modification of using lysis reagent A containing 20% (w/v) Tween® 20 (Fluka) and binding reagent D containing 9% (w/v) Tween® 20 (Fluka).

Figure 2:
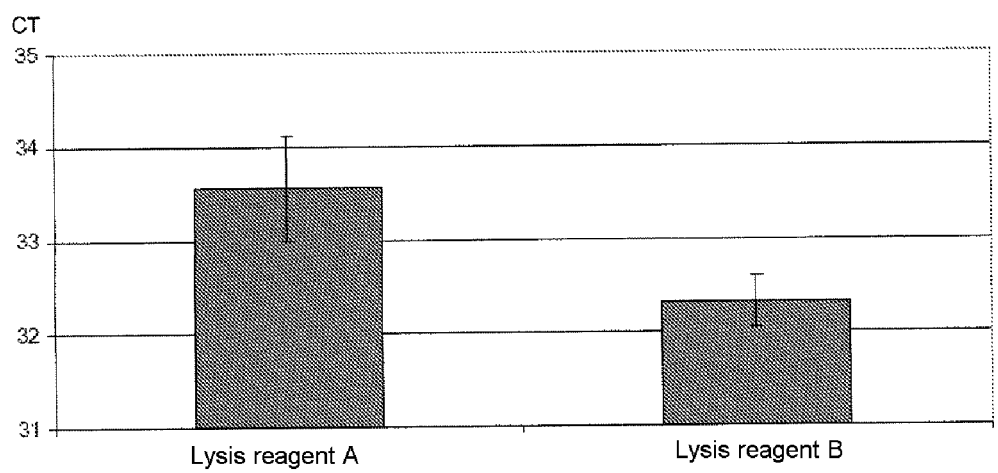
FIG. 2 depicts the averages of CT values after HBV-specific real time PCR of HBV-DNA after carrying out preparations of viral DNA with the lysis reagent B of the invention and the Tween® 20-containing lysis reagent A.

The eluates obtained were subjected in each case to an HBV-specific real time (RT-) PCR, with 24 µl of eluate being used in each case. The averages, depicted in FIG. 2, of the CT values (threshold cycle) which describe the cycle at which the fluorescence begins to increase logarithmically revealed that the extraction using the lysis reagent B and binding reagent C of the invention achieved a higher yield.

EXAMPLE 3: EXTRACTION OF VIRAL DNA AFTER STORAGE OF THE LYSIS REAGENT

The lysis reagents B containing guanidinium isothiocyanate, tris(hydroxymethyl)aminomethane and 20% (w/v) Brij® 58 (Sigma), and A in which Brij® 58 had been replaced with 20% (w/v) Tween® 20 (Fluka) were each stored in sealed vessels at 50° C. for 10 weeks.

The viral nucleic acid was then extracted, using the commercially available automation platform QIAsymphony® (Qiagen), by means of the automated protocol for purifying viral nucleic acid from plasma samples.

According to the protocol described in Example 2, the viral DNA was extracted from in each case 1000 µl of the plasma sample using the commercially available automation platform QIAsymphony® (Qiagen), with, for different mixtures, lysis reagent B containing guanidinium isothiocyanate, tris(hydroxymethyl)aminomethane and 20% (w/v) Brij® 58 (Sigma), and lysis reagent A in which Brij® 58 had been replaced with 20% (w/v) Tween® 20 (Fluka) being stored in each case at 50° C. for 10 weeks. The reference used was a lysis reagent A which was stored at room temperature for about 4 weeks.

We found that the eluates obtained using the lysis reagent A stored at 50° C. were very opaque, while the eluates obtained using the lysis reagent B were clear.

Figure 3:
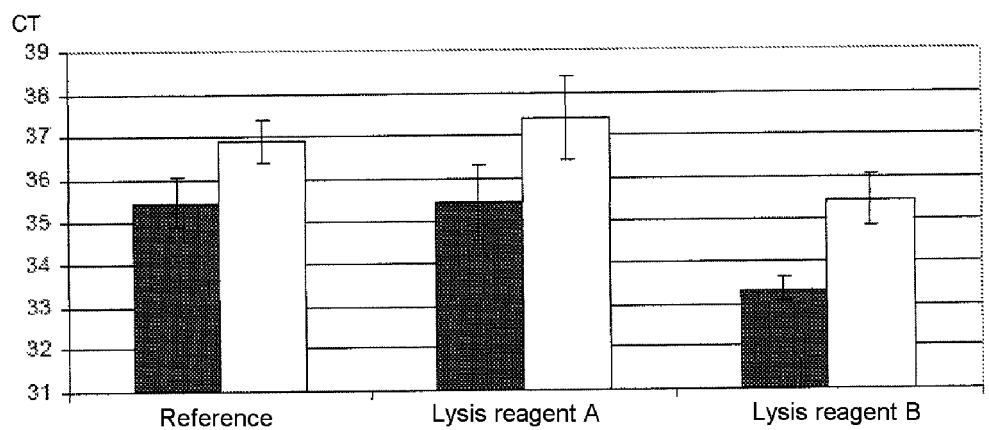
FIG. 3 depicts the averages of CT values after HBV-specific real time PCR of HBV-DNA after carrying out preparations of viral DNA with the lysis reagent B of the invention and the Tween® 20-containing lysis reagent A after 10 weeks of storage at 50° C. Here, a lysis reagent A which was stored at room temperature for about 4 weeks was used as reference. In each case, 6 µl and 24 µl of the eluate were used for the real time PCR, with the results for 6 µl of the eluate being depicted as empty bars and the results for 24 µl of eluate being depicted as filled bars.

In each case, 6 µl and 24 µl of the eluates obtained were subjected to an HBV-specific real time (RT-) PCR. The averages of the CT values, depicted in FIG. 3, revealed that the extraction using the lysis reagent B and binding reagent C of the invention achieved a higher yield.

The invention claimed is:

1. A method for isolating and/or purifying nucleic acids from a nucleic acid-containing biological sample, comprising the following method steps:
   a) lysing the biological sample to release nucleic acid(s) in a lysis composition,
   b) immobilizing the released nucleic acid(s) on a matrix based on one or more silicon oxide compound(s) in a binding composition, wherein the matrix is selected from the group consisting of particles, membranes, and filters,
   c) optionally washing the nucleic acid(s) immobilized on the matrix,
   d) optionally removing the immobilized nucleic acid,
      wherein the lysing and/or immobilizing are carried out in the presence of a lysis and/or binding composition comprising:
      at least one chaotropic compound,
      at least one buffer compound, and
      at least one polyoxyethylene-based non-ionic surfactant which is a polyoxyethylene fatty alcohol ether selected from the group consisting of polyoxyethylene cetyl ether, polyoxyethylene stearyl ether, and polyoxyethylene oleyl ether in the range from ≥3% weight/volume to ≤30% weight/volume, based on the total volume of the composition,
      wherein the immobilizing is optionally carried out in the presence of the binding composition that further comprises a branched or unbranched alkanol, and
      wherein the method further comprises preparing the lysis and/or binding composition using a liquid lysis and/or binding reagent comprising:
      the at least one chaotropic compound,
      the at least one buffer compound, and
      the at least one polyoxyethylene-based non-ionic surfactant.

2. The method according to claim 1, wherein the binding composition further comprises a branched or unbranched alkanol.

3. The method according to claim 1, wherein the polyoxyethylene fatty alcohol ether comprises a polyoxyethylene component containing from 2 to 150 ($CH_2CH_2O$) units.

4. The method according to claim 3, wherein the polyoxyethylene fatty alcohol ether is a polyoxyethylene cetyl ether.

5. The method according to claim 1, wherein the lysis and/or binding composition comprises the polyoxyethylene fatty alcohol ether in the range from ≥3% weight/volume to ≤10% weight/volume, based on the total volume of the composition.

6. The method according to claim 1, wherein the lysis and/or binding composition comprises the polyoxyethylene fatty alcohol ether in the range from ≥3.2% weight/volume to ≤8% weight/volume, based on the total volume of the composition.

7. The method according to claim 1, wherein the chaotropic compound is a guanidinium salt.

8. The method according to claim 7, wherein the guanidinium salt is selected from the group consisting of guanidinium hydrochloride, guanidinium thiocyanate, and guanidinium isothiocyanate.

9. The method according to claim 1, wherein the lysis and/or binding composition comprises the chaotropic compound in a range of ≥0.1 M to ≤10 M.

10. The method according to claim 1, wherein the lysis and/or binding composition comprises the chaotropic compound in a range of ≥1 M to ≤8 M.

11. The method according to claim 1, wherein the buffer compound is selected from the group consisting of tris (hydroxymethyl)aminomethane, N-(tri (hydroxymethyl)methyl)glycine, N,N-bis(2-hydroxyethyl)glycine, 3-(N-morpholino)-propanesulphonic acid, N-(2-hydroxyethyl) piperazine-N'-(2-ethanesulphonic acid), piperazine-1,4-bis (2-ethanesulphonic acid), N-cyclohexyl-2-aminoethanesulphonic acid, 2-(N-morpholino) ethanesulphonic acid, 3-(N-morpholino) propanesulphonic acid and phosphate buffer.

12. The method according to claim 1, wherein the liquid lysis and/or binding reagent is an aqueous solution having a pH in the range from ≥6 to ≤11.

13. The method according to claim 1, wherein the liquid lysis and/or binding reagent is an aqueous solution having a pH in the range from ≥7 to ≤10.

14. The method according to claim 1, wherein the biological sample is selected from the group consisting of blood, plasma, serum, mouth, throat and nose rinses, bronchoalveolar lavages, urine, cerebral fluid, sputum, saliva, stool, aspirates, smears/swabs, biopsies, tissue or bone marrow samples, and cell cultures.

* * * * *